US008758255B2

(12) United States Patent
Park et al.

(10) Patent No.: US 8,758,255 B2
(45) Date of Patent: Jun. 24, 2014

(54) METHODS FOR FIELD OF VIEW CONTROL IN IMAGING SYSTEMS

(75) Inventors: Byong-Ho Park, Cincinnati, OH (US); Oren Levy, Emerald Hills, CA (US); Frank Hubbard, San Francisco, CA (US)

(73) Assignee: Volcano Corporation, San Diego, CA (US)

( * ) Notice: Subject to any disclaimer, the term of this patent is extended or adjusted under 35 U.S.C. 154(b) by 683 days.

(21) Appl. No.: 12/877,560

(22) Filed: Sep. 8, 2010

(65) Prior Publication Data
US 2011/0218437 A1 Sep. 8, 2011

Related U.S. Application Data

(60) Provisional application No. 61/240,597, filed on Sep. 8, 2009.

(51) Int. Cl.
*A61B 8/12* (2006.01)
(52) U.S. Cl.
USPC ............................ 600/462; 600/445; 600/459
(58) Field of Classification Search
USPC .................. 600/437, 443, 444, 445, 459, 462
See application file for complete search history.

(56) References Cited

U.S. PATENT DOCUMENTS

| 4,106,492 A | 8/1978 | Schuette et al. |
| 5,090,414 A * | 2/1992 | Takano ........................ 600/461 |
| 5,181,514 A | 1/1993 | Solomon et al. |
| 5,467,779 A | 11/1995 | Smith et al. |
| 6,409,669 B1 | 6/2002 | Hager et al. |
| 2003/0055338 A1 | 3/2003 | Steininger et al. |
| 2006/0173330 A1 * | 8/2006 | Kim .............................. 600/445 |
| 2007/0249937 A1 | 10/2007 | Hasegawa et al. |
| 2008/0007408 A1 * | 1/2008 | Hwang et al. .............. 340/572.1 |

FOREIGN PATENT DOCUMENTS

WO WO 2009/140641 * 5/2009

OTHER PUBLICATIONS

International Searching Authority/Korean Intellectual Property Office, "Notification of Transmittal of the International Search Report and the Written Opinion of the International Searching Authority, or the Declaration," for PCT/US2010/048122, mailed Apr. 8, 2011, 10 pages.

* cited by examiner

*Primary Examiner* — Christopher Cook
(74) *Attorney, Agent, or Firm* — Haynes and Boone, LLP

(57) ABSTRACT

Devices, systems, and methods for controlling the field of view in imaging systems are provided. For example, in one embodiment an imaging system includes a flexible elongate sized and shaped for use within an internal structure of a patient, an imaging transducer positioned within the distal portion of the flexible elongate member, and a monitor positioned within the distal portion of the flexible elongated member and configured to generate a feedback signal indicative of a position of the imaging transducer relative to the transducer's motion profile. The imaging system may also include a controller in communication with the monitor and configured to adjust a control signal based on the feedback signal in order to achieve a desired field of view for the imaging transducer.

22 Claims, 26 Drawing Sheets

METHODS FOR FIELD OF VIEW CONTROL IN IMAGING SYSTEMS

CROSS-REFERENCE TO RELATED APPLICATION

This application claims priority under 35 U.S.C. §119 to U.S. Provisional Patent Application No. 61/240,597, filed Sep. 8, 2009, titled "Devices and Methods for Field of View Control in Miniature Ultrasonic Imaging Mechanisms," the entire disclosure of which is hereby incorporated by reference in its entirety.

TECHNICAL FIELD

Embodiments of the present disclosure relate generally to imaging systems and, more particularly, to imaging systems sized for use within human vasculature. In some instances, the devices, systems, and methods of the present disclosure are directed to controlling the field of view of such imaging systems.

BACKGROUND

In the United States and many other countries, heart disease is a leading cause of death and disability. One particular kind of heart disease is atherosclerosis, which involves the degeneration of the walls and lumen of the arteries throughout the body. Scientific studies have demonstrated the thickening of an arterial wall and eventual encroachment of the tissue into the lumen as fatty material builds upon the vessel walls. The fatty material is known as "plaque." As the plaque builds up and the lumen narrows, blood flow is restricted. If the artery narrows too much, or if a blood clot forms at an injured plaque site (lesion), flow is severely reduced, or cut off and consequently the muscle that it supports may be injured or die due to a lack of oxygen. Atherosclerosis can occur throughout the human body, but it is most life threatening when it involves the coronary arteries which supply oxygen to the heart. If blood flow to the heart is significantly reduced or cut off, a myocardial infarction or "heart attack" often occurs. If not treated in sufficient time, a heart attack often leads to death.

The medical profession relies upon a wide variety of tools to treat heart disease, ranging from drugs to open heart "bypass" surgery. Often, a lesion can be diagnosed and treated with minimal intervention through the use of catheter-based tools that are threaded into the coronary arteries via the femoral artery in the groin. For example, one treatment for lesions is a procedure known as percutaneous transluminal coronary angioplasty (PTCA) whereby a catheter with an expandable balloon at its tip is threaded into the lesion and inflated. The underlying lesion is re-shaped, and hopefully, the lumen diameter is increased to improve blood flow. Such techniques have traditionally relied on CT scans performed before surgery and angiograms during surgery to identify important anatomical features of the vasculature associated with the interventions. However, the information from a CT scan is often inaccurate at the time of surgery since the aneurysm is continually evolving over time.

Further, interventional procedures in the intracardiac space are continually developing. In that regard, structural heart procedures, including but not limited to valve replacement, valve repair, catheter ablation for arrhythmia, left atrial appendage (LAA) procedures, patent foramen ovale (PFO) procedures, and atrial septal defect procedures, also rely on imaging of the corresponding heart structures. Without accurate and detailed images of the associated structures, these interventional procedures in the intracardiac space become difficult, if not impossible, to perform successfully.

In recent years, techniques have been developed for obtaining detailed information about coronary and peripheral vessels as well as the intracardiac structures. For example, Intravascular Ultrasound (IVUS) and Intracardiac Echocardigraphy (ICE) techniques employ one or more very small transducers arranged towards the end of a catheter to provide electronically transduced echo signals to an external imaging system in order to produce a two or three-dimensional image of the lumen, the vessel tissue, and/or the tissue surrounding the vessel. Often these high quality images are generated in substantially real time. The images from these techniques allow a user to view the form and structure of a site rather then merely determining that blood is flowing.

In some instances, these devices rely on mechanical movement of an imaging transducer (e.g., an ultrasound transducer) in order to repeatedly sample a multi-dimensional space. In order to provide accurate information, effort is made to coordinate the transducer motion and the associated ultrasound acquisition. In that regard, the external imaging system typically controls the movement of the transducer. For example, in some instances the displacement of the imaging transducer is directly correlated to the voltage or current waveform of a control signal generated by the external imaging system.

While the existing devices and methods have been generally adequate for their intended purposes, they have not been entirely satisfactory in all respects. The devices, systems, and associated methods of the present disclosure overcome one or more of the shortcomings of the prior art.

SUMMARY

Devices, systems, and methods for controlling the field of view in imaging systems are provided.

DETAILED DESCRIPTION

Figure 1:
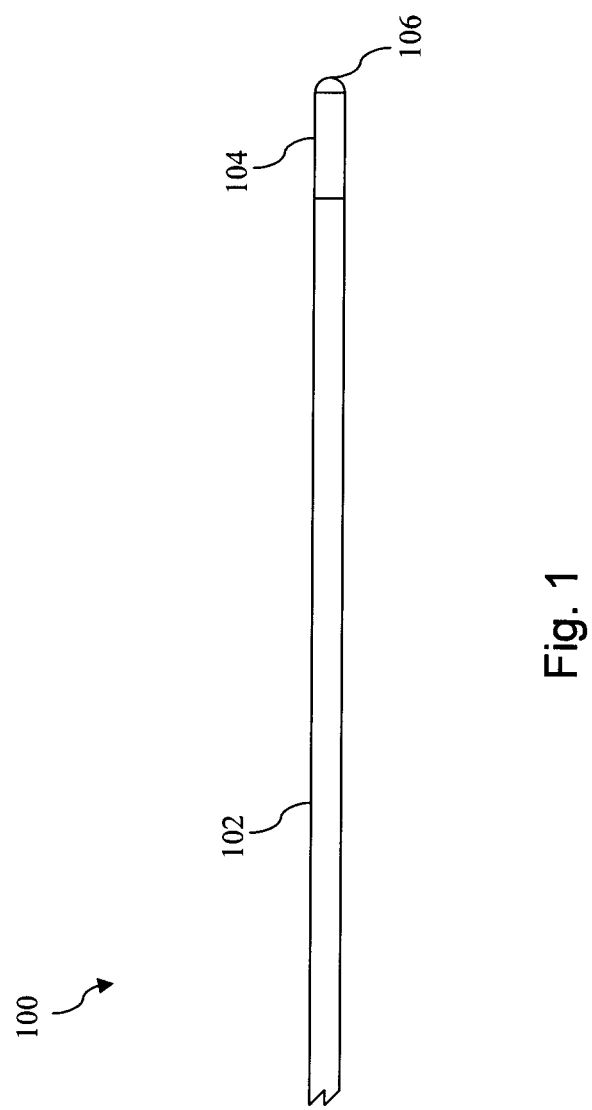
FIG. 1 is a diagrammatic schematic view of a portion of an elongated member of an imaging system according to one aspect of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

Figure 2:
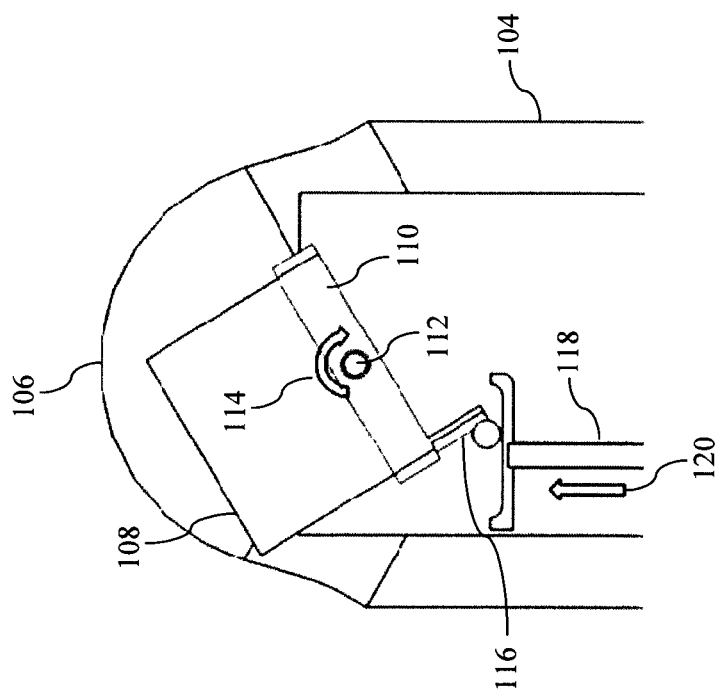
FIG. 2 is a partial cross-sectional side view of a distal end portion of the elongated member of FIG. 1 illustrating a transducer element of the imaging system in a first orientation.
Figure 3:
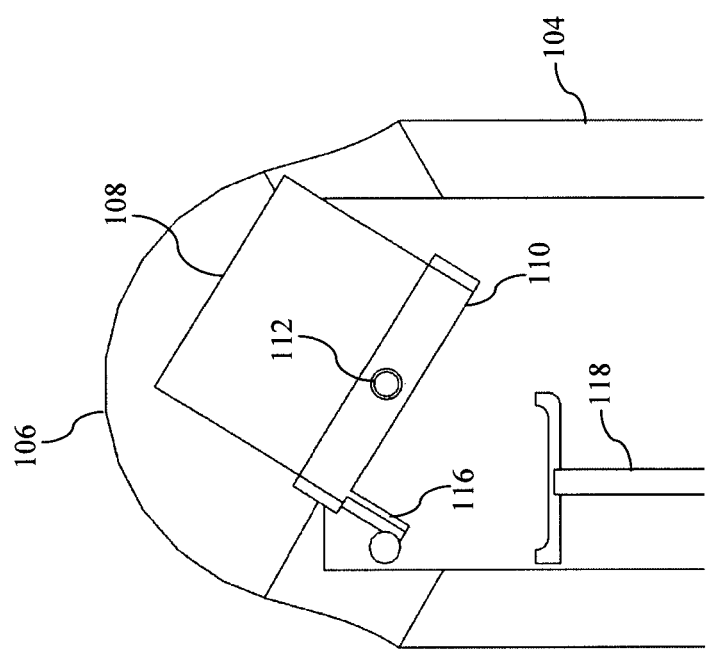
FIG. 3 is a partial cross-sectional side view of the distal end portion of the elongated member similar to that of FIG. 2 but illustrating the transducer element in a second orientation.

Referring to FIGS. 1-3, shown therein are aspects of an elongated member 100 of an imaging system according to an embodiment of the present disclosure. More specifically, FIG. 1 is a diagrammatic schematic view of a portion of the elongated member 100; FIG. 2 is a partial cross-sectional side view of a distal end portion of the elongated member 100, illustrating a transducer element of the imaging system in a first orientation; and FIG. 3 is a partial cross-sectional side view of the distal end portion of the elongated member 100, similar to that of FIG. 2, but illustrating the transducer element in a second orientation.

As shown in FIG. 1, the elongated member 100 includes a flexible body 102 having a distal housing portion 104 extending to a distal tip 106. As shown in FIG. 2, a transducer 108 is disposed within the distal housing portion 104 adjacent the distal tip 106. In some instances the transducer 108 is an ultrasound transducer. In the illustrated embodiment, the transducer 108 is mounted on a platform 110 that is configured to rotate about an axis defined by a pivot pin 112 extending through a portion of the platform 110. In that regard, transducer 108 rotates—in the direction of arrow 114—from an initial orientation (shown in FIG. 2) to a fully-rotated orientation (shown in FIG. 3). From the fully-rotated orientation, the transducer rotates—in the direction opposite of arrow 114—back to the initial orientation. This process is repeated to cause oscillation of the transducer 108.

In the illustrated embodiment, an interface arm 116 extends proximally from the platform 110 and interfaces with an actuator 118 to facilitate oscillation of the transducer 108. As shown in FIG. 2, when the transducer 108 is in the initial position advancement of the actuator 118 distally, as indicated by arrow 120, urges the interface arm 116 distally, which causes the platform 110 to rotate about the pivot pin 112. Rotation of the platform 110 sweeps the transducer 108 from the initial position (FIG. 2) to the fully-rotated position (FIG. 3).

While FIGS. 2 and 3 illustrate the transducer 108 being oscillated, in other instances the transducer 108 is maintained in a fixed position and a mirror or other reflective element is oscillated. In that regard, the mirror or other reflective element reflects the signals generated by the fixed transducer (e.g., acoustic waves associated with ultrasound imaging) such that the signals are swept through the motion profile in a manner similar to when the transducer itself is oscillated. In some instances, the fixed transducer and reflector are configured in a manner similar to the embodiments described U.S. Pat. No. 7,658,715, titled "MINIATURE ACTUATOR MECHANISM FOR INTRAVASCULAR IMAGING," which is hereby incorporated by reference in its entirety.

Figure 26:
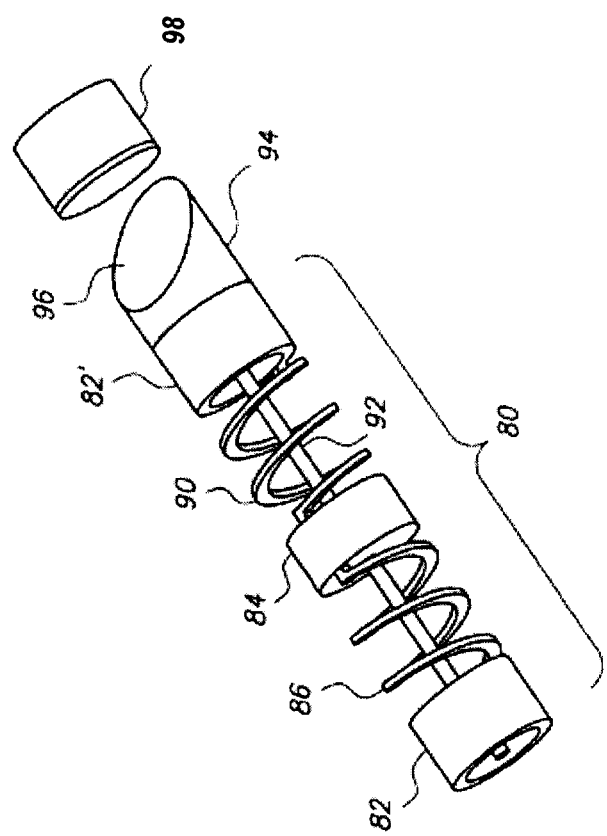
FIG. 26 is a perspective view showing an actuator mechanism with an ultrasound reflector connected by a connecting arm, with an ultrasound transducer aligned with the reflector.

For example, FIG. 26 illustrates a preferred embodiment of the invention of U.S. Pat. No. 7,658,715. Shown in FIG. 26 is an actuator mechanism 80 which has two anchors 82 and 82', a moveable element 84 connected to the anchor 82 and 82' by an SMA actuator 86 and a deformable component 90. A connecting arm 92 connects the moveable element 84 to an ultrasound energy reflector 94. The reflector 94 has a surface 96 which is oriented to reflect ultrasound energy to and from an ultrasound transducer 98.

In general, the elongate member 100 is sized and shaped for use within an internal structure of a patient, including but not limited to a patient's arteries, veins, heart chambers, neurovascular structures, GI track, bronchials, organs, and/or other areas where internal imaging of patient anatomy is desirable. In that regard, depending on the particular medical application, the elongate member 100 is configured for use in cardiology procedures, neurovascular procedures, pulmonology procedures, endoscopy procedures, colonoscopy procedures, natural orifice procedures (such as Natural Orifice Translumenal Endoscopic Surgery (NOTES)), and/or other medical procedures.

Accordingly, in some embodiments the elongate member 100 takes the form of a guidewire or catheter. In some instances, the imaging system as a whole, the elongate member 100, the actuator 118, and/or other aspects of the imaging system are similar to those described in U.S. Pat. No. 5,379,772, titled "FLEXIBLE ELONGATE DEVICE HAVING FORWARD LOOKING ULTRASONIC IMAGING," U.S. Pat. No. 7,115,092, titled "TUBULAR COMPLIANT MECHANISMS FOR ULTRASONIC IMAGING SYSTEMS AND INTRAVASCULAR INTERVENTIONAL DEVICES," and/or U.S. Pat. No. 7,658,715, titled "MINIATURE ACTUATOR MECHANISM FOR INTRAVASCULAR IMAGING," each of which is hereby incorporated by reference in its entirety.

To function most effectively, the data acquired with the transducer 108 must be coordinated with the transducer's motion. Accordingly, in some aspects, the present disclosure is directed to feedback control mechanisms that monitor and control the motion of the transducer and, thereby, control the resulting field of view of the imaging system. In that regard, aspects of the present disclosure increase the accuracy and reproducibility of the transducer's motion. This results in improved clarity and accuracy in the resulting images provided by the imaging systems.

Figure 4:
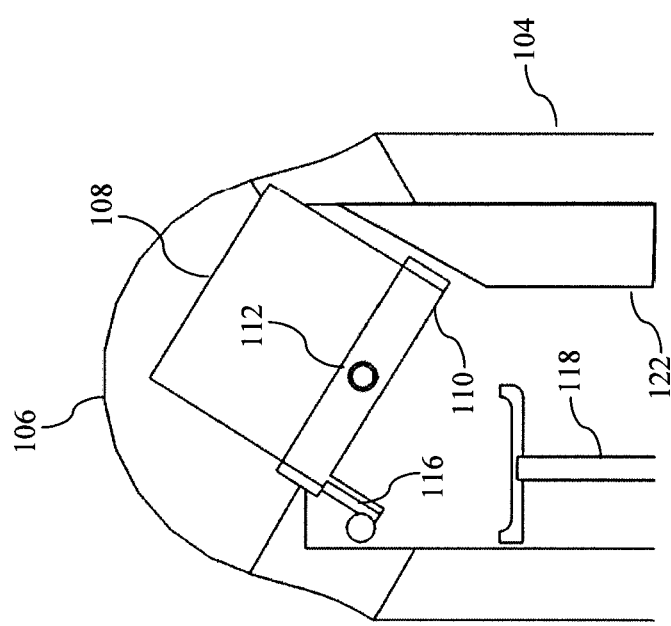
FIG. 4 is a partial cross-sectional side view of the distal end portion of an elongated member similar to that of FIG. 3, but illustrating another embodiment of the present disclosure.
Figure 5:
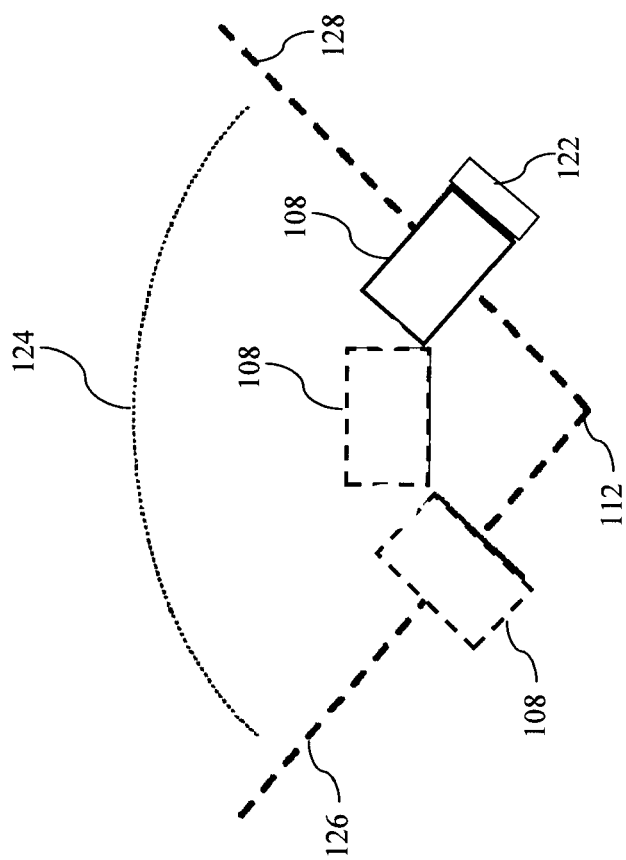
FIG. 5 is a diagrammatic schematic view of a motion path of a transducer element of an imaging system according to one aspect of the present disclosure.

Referring to FIGS. 4 and 5, shown therein is an embodiment elongated member configured for monitoring transducer motion according to an aspect of the present disclosure. In particular, FIG. 4 is a partial cross-sectional side view of the distal end portion of an elongated member, while FIG. 5 is a diagrammatic schematic view of a motion path of a transducer element of the elongated member of FIG. 4. Referring more specifically to FIG. 4, as shown the illustrated distal end portion is similar to the distal end portion of elongated member 100 (shown in FIG. 3) in many respects. Accordingly, the same reference numerals have been utilized to label similar parts. However, the distal end portion of FIG. 4 includes an additional element, namely monitor 122. In general, monitor 122 is a mechanism configured to monitor one or more aspects of the motion of transducer 108. In that regard, several examples of suitable configurations for monitor 122 are described below with respect to FIGS. 6-18. However, it is understood that any other mechanical, electrical, optical, electromechanical, optoelectronic, and/or other monitoring device, including combinations thereof, may be utilized.

In some embodiments, the monitor 122 monitors the position of the transducer 108 during its motion profile. In that regard, FIG. 5 illustrates an exemplary motion profile of the transducer 108. As shown, the transducer 108 pivots about the pivot pin 112 and travels across an angle 124 between a starting orientation (represented by axis 126 and the transducer 108 shown in phantom on the far left of the drawing) and an ending orientation (represented by axis 128 and the transducer 108 shown on the far right of the drawing). In that regard, the angle 124 that the transducer 108 travels between the starting orientation and the ending orientation is generally between about 1 degree and about 400 degrees, depending on the imaging application. In some instances, the angle 124 is between about 25 degrees and about 360 degrees. It is understood, however, that the present disclosure is applicable to any amount of transducer rotation and no limitation is intended by these exemplary ranges.

As noted above, the monitor 122 monitors the position of the transducer 108 during its motion profile. In that regard, in some instances the monitor 122 is configured to detect if and/or when the transducer 108 reaches a certain point of its motion profile. For example, in some instances the monitor 122 is configured to detect if and/or when the transducer 108 reaches the ending orientation, as represented by axis 128. In other instances, the monitor 122 is configured to detect if and/or when the transducer 108 reaches other points along its motion profile, including but not limited to the starting orientation, a mid-point orientation (represented by transducer 108 shown in phantom in the middle of the drawing), and/or other orientations along the motion profile. In that regard, the boundaries of the motion profile of the transducer 108 are illustrated in FIG. 5 by axes 126 and 128. These boundaries are representative of the desired motion profile of the transducer during use. However, it is understood that the actual motion profile of the transducer may vary during use and, therefore, may travel beyond the boundaries of the desired motion profile. Accordingly, in some instances, the monitor is configured to detect if and/or when the transducer 108 reaches a point beyond the desired motion profile. Further, in some instances, the monitor 122 is configured to continuously track the position of the transducer 108 relative to a certain point of the motion profile.

In some embodiments, the monitor 122 is configured to detect if and/or when the transducer 108 reaches two or more points along the motion profile, rather than a single point. In that regard, in some embodiments the monitor 122 includes a single component configured to detect if and/or when the transducer 108 reaches the points along the motion profile. In other embodiments monitor 122 includes two or more components, each configured to monitor a single point along the motion profile such that the components collectively monitor the two or more points along the motion profile. Where the monitor 122 includes two or more components, one or more of the components may be spaced apart from one or more of the other components or all of the components may be positioned adjacent to one another.

Exemplary embodiments of configurations for monitor 122 will now be described in the context of FIGS. 6-18. For the sake of clarity and simplicity, the discussion herein will use the ending orientation of the transducer (represented by axis 128 and the transducer 108 shown on the far right of FIG. 5) as the detection point along the motion profile. In some instances the monitor 122 takes the form of a switch that changes states (for example, from on-to-off or from off-to-on) when the transducer 108 reaches the ending orientation of its motion profile. In that regard, FIGS. 6-13 illustrate various embodiments of switches suitable for use as monitor 122.

Figure 6:
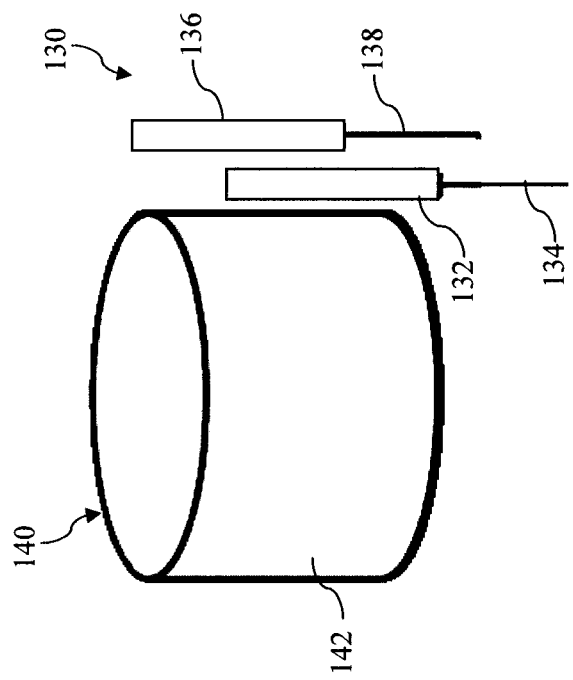
FIG. 6 is a diagrammatic perspective view of a switch configuration according to one embodiment of the present disclosure, where the switch configuration is illustrated in an open position.
Figure 7:
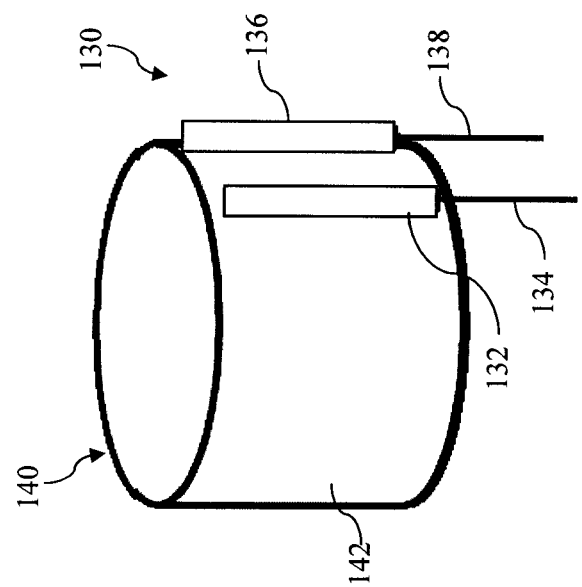
FIG. 7 is a diagrammatic perspective view of the switch configuration of FIG. 6, but illustrating the switch configuration in a closed position.

Referring more specifically to FIGS. 6 and 7, shown therein is a switch 130 according to one embodiment of the present disclosure. More specifically, FIG. 6 illustrates the switch 130 in an open position, while FIG. 7 illustrates the switch 130 in a closed position. The switch 130 includes an electrode 132 coupled to an electrical conductor 134 and an electrode 136 coupled to an electrical conductor 138. In that regard, the conductors 134, 138 connect the electrodes 132, 136 to the imaging system such that the signals generated by the switch 130 can be communicated to a portion of the imaging system for processing. As shown in FIG. 6, when the transducer 140 is spaced from the switch 130 along its motion profile, the electrodes 132, 136 are spaced apart from one another in a fixed orientation such that there is an open space between the electrodes 132, 136. Since the electrodes 132, 136 are stationary with respect to one another, switch 130 may be referred to as a static switch. Referring to FIG. 7, when the transducer 140 reaches the ending orientation of its motion profile, an outer surface 142 of the transducer connects the electrodes 132, 136. In that regard, at least the portion of the outer surface 142 filling the gap between the electrodes 132, 136 is formed of a conductive material so that the switch 130 is turned on when the conductive surface contacts the electrodes. Accordingly, the switch 130 is activated whenever the transducer 140 reaches its ending orientation and contacts the electrodes 132, 136.

While the transducer 140 has been described as being the element that activates the switch 130, it is fully understood that the conductive surface may be part of some other element that has a known orientation relative to the transducer, such as a mounting platform or other component associated with the transducer. Accordingly, while the remaining embodiments of monitors will similarly be described in the context of a transducer, it is understood that no limitation is intended thereby and that use of any other element having a known orientation (either fixed or predictably variable) is expressly within the scope of the present disclosure. In that regard, it is also understood that the monitors described in the context of moving transducers are equally applicable to embodiments where the transducer is maintained in a fixed position and a reflective element is moved. In such embodiments, the monitor is utilized to monitor a position of the reflective element or any other element having a known orientation (either fixed or predictably variable) with respect to the reflective element.

Figure 8:
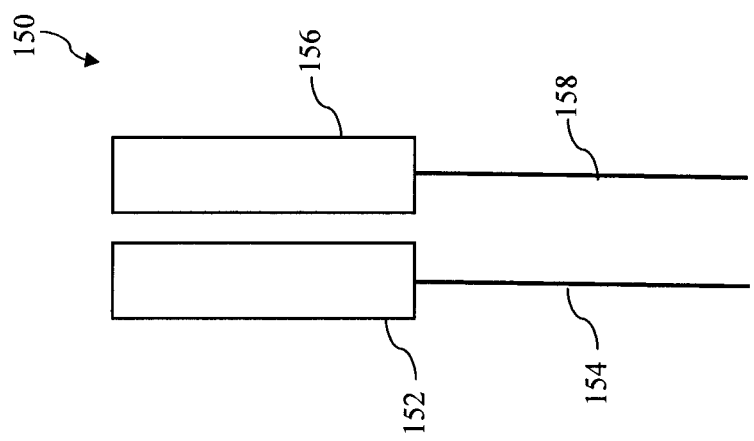
FIG. 8 is a diagrammatic perspective view of a switch configuration according to another embodiment of the present disclosure, where the switch configuration is illustrated in an open position.
Figure 9:
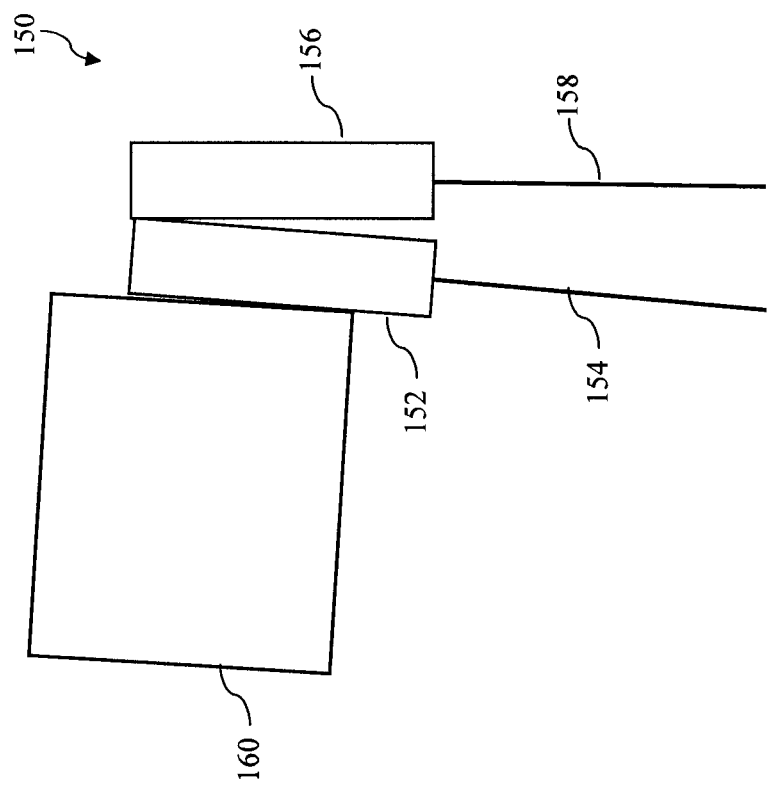
FIG. 9 is a diagrammatic perspective view of the switch configuration of FIG. 8, but illustrating the switch configuration in a closed position.

Referring now to FIGS. 8 and 9, shown therein is a switch 150 according to another embodiment of the present disclosure. More specifically, FIG. 8 illustrates the switch 150 in an open position, while FIG. 9 illustrates the switch 150 in a closed position. The switch 150 includes an electrode 152 coupled to an electrical conductor 154 and an electrode 156 coupled to an electrical conductor 158. In that regard, the conductors 154, 158 connect the electrodes 152, 156 to the imaging system such that the signals generated by the switch 150 can be communicated to a portion of the imaging system for processing. As shown in FIG. 8, in the open position the electrodes 152, 156 are spaced apart from one another such that there is an open space between the electrodes 152, 156. In the illustrated embodiment, at least electrode 152 and an associated portion of electrical conductor 154 are movable with respect to electrode 156 such that the gap between the electrodes can be closed to turn the switch on. In that regard, as shown in FIG. 9, when the transducer 160 reaches the ending orientation of its motion profile it displaces electrode 152 into contact with electrode 156 to close the circuit and turn the switch on. Once the transducer 160 continues along its motion profile back toward the starting orientation, the electrode 152 will return to open position illustrated in FIG. 8. In that regard, the electrode 152 is biased to the open position. In some instances, a spring, elastic element, or other resiliently flexible component (not shown) biases the electrode 152 to the open position.

Figure 10:
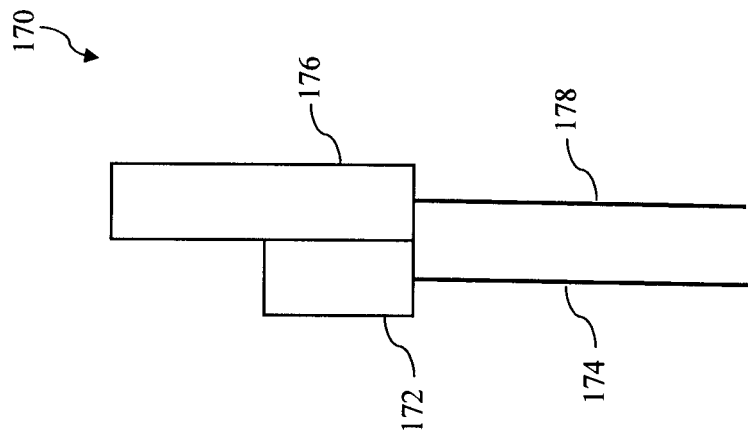
FIG. 10 is a diagrammatic perspective view of a switch configuration according to another embodiment of the present disclosure, where the switch configuration is illustrated in a closed position.
Figure 11:
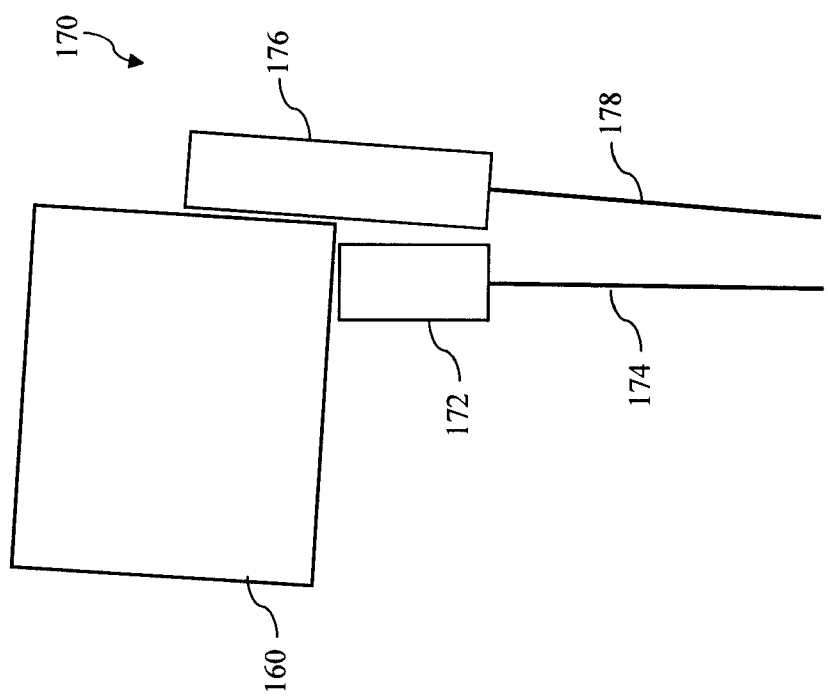
FIG. 11 is a diagrammatic perspective view of the switch configuration of FIG. 10, but illustrating the switch configuration in an open position.

Referring now to FIGS. 10 and 11, shown therein is a switch 170 according to another embodiment of the present disclosure. More specifically, FIG. 10 illustrates the switch 170 in a closed position, while FIG. 11 illustrates the switch 170 in an open position. The switch 170 includes an electrode 172 coupled to an electrical conductor 174 and an electrode 176 coupled to an electrical conductor 178. In that regard, the conductors 174, 178 connect the electrodes 172, 176 to the imaging system such that the signals generated by the switch 170 can be communicated to a portion of the imaging system for processing. As shown in FIG. 10, in the closed position the electrodes 172, 176 are connected such that the switch is on. In the illustrated embodiment, at least electrode 176 and an associated portion of electrical conductor 178 are movable with respect to electrode 172 such that a gap can be created between the electrodes to turn the switch off. In that regard, as shown in FIG. 11, when the transducer 160 reaches the ending orientation of its motion profile it displaces electrode 176 such that it is spaced from electrode 172 to open the circuit and turn the switch off. Once the transducer 160 continues along its motion profile back toward the starting orientation, the electrode 176 will return to open position illustrated in FIG. 10. In that regard, the electrode 176 is biased to the closed position. In some instances, a spring, elastic element, or other resiliently flexible component (not shown) biases the electrode 176 to the closed position.

Figure 12:
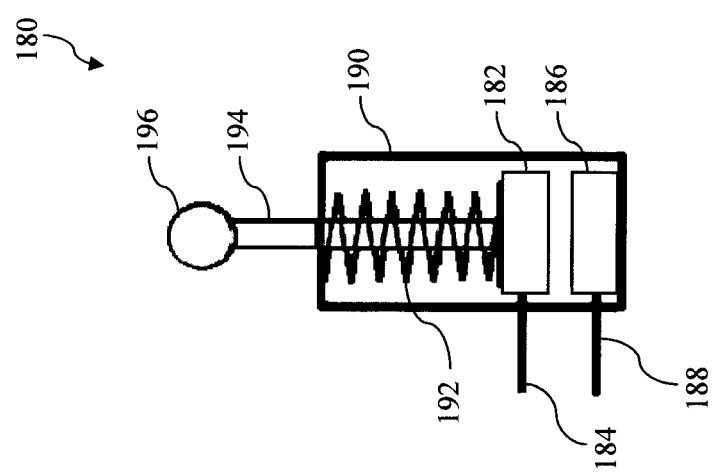
FIG. 12 is a diagrammatic perspective view of a switch configuration according to another embodiment of the present disclosure, where the switch configuration is illustrated in an open position.
Figure 13:
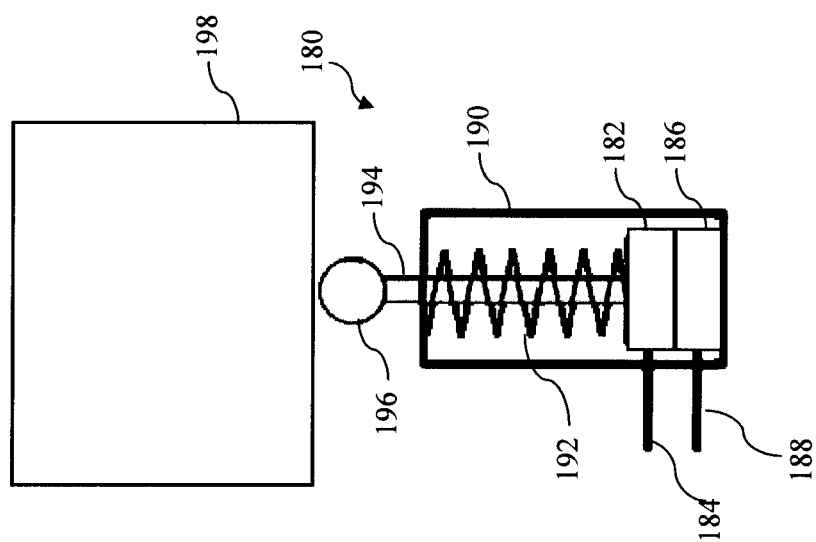
FIG. 13 is a diagrammatic perspective view of the switch configuration of FIG. 12, but illustrating the switch configuration in a closed position.

Referring now to FIGS. 12 and 13, shown therein is a switch 180 according to another embodiment of the present disclosure. More specifically, FIG. 12 illustrates the switch 180 in an open position, while FIG. 13 illustrates the switch 180 in a closed position. The switch 180 includes an electrode 182 coupled to an electrical conductor 184 and an electrode 186 coupled to an electrical conductor 188. In that regard, the conductors 184, 188 connect the electrodes 182, 186 to the imaging system such that the signals generated by the switch 180 can be communicated to a portion of the imaging system for processing. As shown in FIG. 12, in the open position the electrodes 182, 186 are spaced apart from one another within housing 190 such that there is an open space between the electrodes 182, 186. In the illustrated embodiment, electrode 186 is fixedly mounted to a wall of the housing 190 while electrode 182 and an associated portion of electrical conductor 184 are movable with respect to electrode 186 such that the gap between the electrodes can be closed to turn the switch on. In that regard, a resiliently flexible component 192, such as a spring, elastic element, or other resiliently flexible component, biases the electrode 182 away from electrode 186 and toward the open position. The electrode 182 is coupled, either directly or indirectly, to a shaft 194 extending through the housing. A contact member 194 at the end of the shaft is configured to interface with a transducer 198 when the transducer reaches the ending orientation of its motion profile, as shown in FIG. 13, such that the electrode displaces the shaft 194 that, in turn, displaces electrode 182 into contact with electrode 186 to close the circuit and turn the switch on. Once the transducer 198 continues along its motion profile back toward the starting orientation, the resiliently flexible component will force the electrode 182 back to the open position illustrated in FIG. 12.

Figure 14:
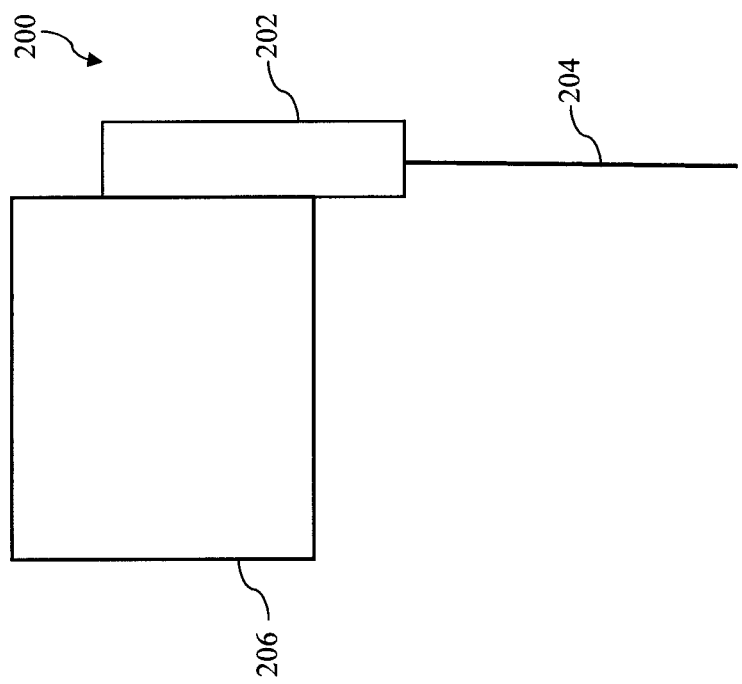
FIG. 14 is a diagrammatic perspective view of a sensor configuration according to an embodiment of the present disclosure.

Referring now to FIG. 14, shown therein is a pressure monitor 200 according to an embodiment of the present disclosure. The pressure monitor 200 includes a pressure sensor 202 and an associated electrical conductor 204. In that regard, the conductor 204 connects the pressure sensor to the imaging system such that the signals generated by the pressure sensor 202 can be communicated to a portion of the imaging system for processing. In that regard, the pressure sensor 202 monitors the amount of pressure induced when the transducer 206 reaches a full field of view. In that regard, in some instances a certain level of pressure is associated with the desired field of view. The pressure sensor 202 sends electrical signals indicative of the amount of pressure induced by the transducer 206. Accordingly, the system can recognize when a threshold level of pressure is reached that corresponds to the transducer 206 reaching the full field of view. This allows the pressure monitor 200 to function in a binary manner, similar to the switches described above. Further, in some instances the system is further configured to recognize when the induced pressure exceeds a maximum desired threshold for a particular field of view. This, in effect, allows the system to determine through the values provided form the pressure sensor 202 whether the transducer 206 is operating within a desired pressure range associated with the intended full field of view. Accordingly, the system can increase and/or decrease the voltage/current being supplied to the actuator in order to maintain the transducer motion profile within the desired full field of view on a consistent basis.

Figure 15:
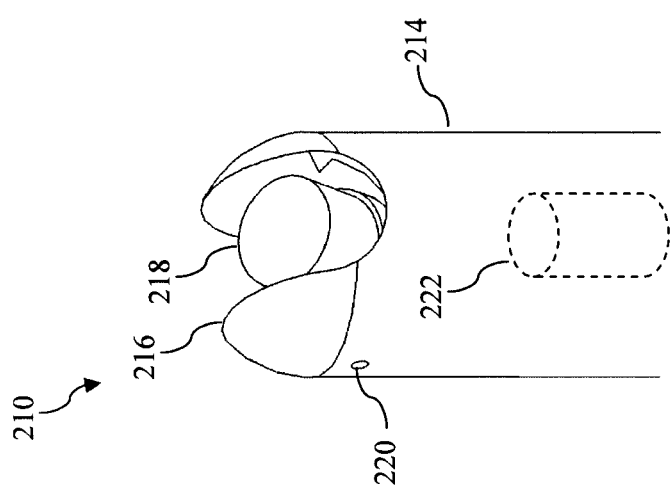
FIG. 15 is a diagrammatic perspective view of a sensor configuration according to another embodiment of the present disclosure.

Referring now to FIG. 15, shown therein is a distal portion of an elongated member 210 according to an embodiment of the present disclosure. The distal portion of the elongated member 210 includes a housing 214 extending to a distal tip 216. Further, a transducer 218 is positioned within the distal portion of the elongated member 210 and pivots about a pivot pin 220. The elongated member 210 also includes a sensing element 222 that is spaced from the motion profile of the transducer 218 and its associated components such that the sensing element is not directly contacted by any components during the motion profile of the transducer 218. In the illustrated embodiment, the sensing element 222 is positioned proximally of the pivot pin 220. In other embodiments, the sensing element 222 is positioned distally of the pivot pin, but still out contact of the motion profile of the transducer 218. The sensing element 222 is configured to monitor the motion profile of the transducer 218.

In one embodiment, the sensing element 222 is a vibration sensor, such as an accelerometer. In that regard, the vibration sensor can be spaced proximally from the transducer 218, allowing increased flexibility in the size and shape of the vibration sensor. In some instances, the vibration sensor is positioned adjacent the proximal portion of the elongated member. The vibration sensor detects whether the transducer 218 reaches the ending orientation of the scanning motion profile by monitoring the intensity of the vibration imparted on the housing 214. In that regard, the vibration sensor monitors the amount of vibration induced when the transducer 218 reaches a full field of view. In that regard, in some instances a certain level of vibration is associated with the desired field of view. The vibration sensor sends electrical signals indicative of the amount of vibration induced by the transducer 218. Accordingly, the system can recognize when a threshold level of vibration is reached that corresponds to the transducer 218 reaching the full field of view. This allows the vibration sensor to function in a binary manner. Further, in some instances the system is further configured to recognize when the induced vibration exceeds a maximum desired threshold for a particular field of view. This, in effect, allows the system to determine through the values provided from the vibration sensor whether the transducer 218 is operating within a desired range of vibration associated with the intended full field of view. Accordingly, the system can increase and/or decrease the voltage/current being supplied to the actuator in order to maintain the transducer motion profile within the desired full field of view on a consistent basis.

Figure 16:
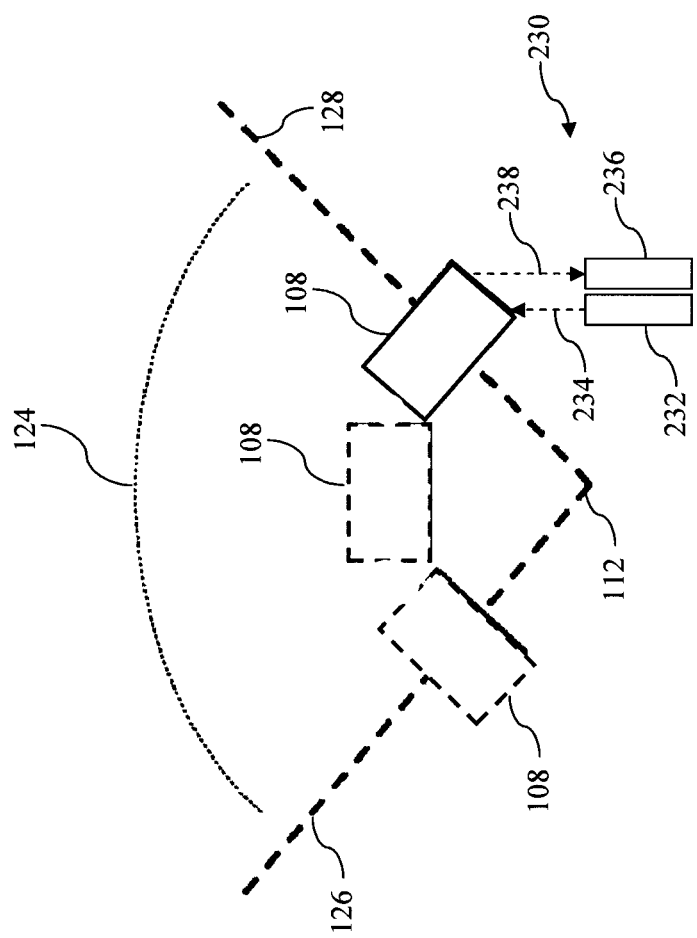
FIG. 16 is a diagrammatic schematic view of a motion path of a transducer element of an imaging system illustrated with an optical sensor according to one embodiment of the present disclosure.
Figure 17:
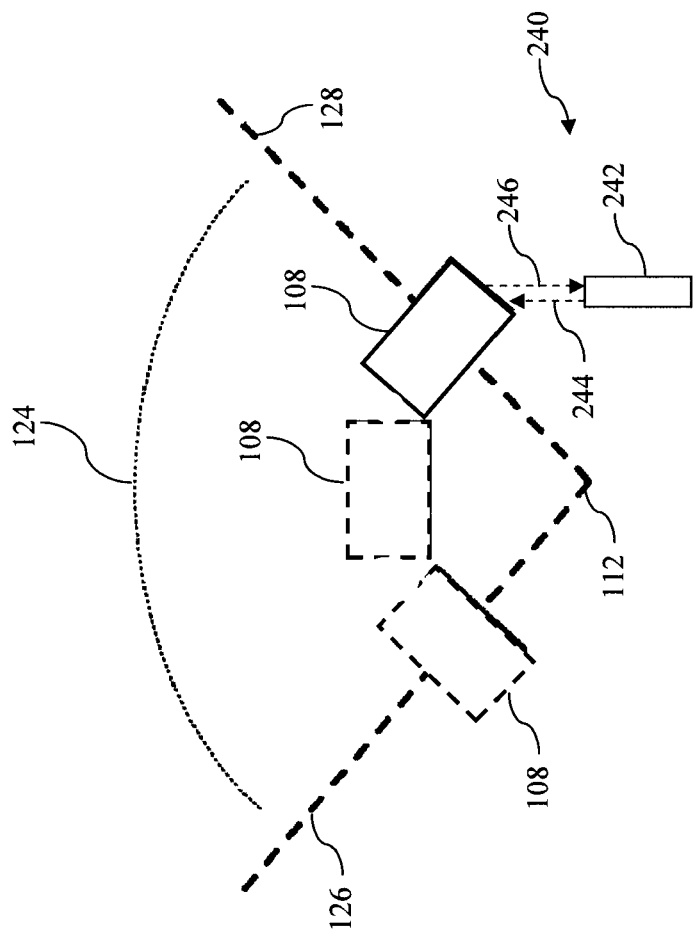
FIG. 17 is a diagrammatic schematic view of a motion path of a transducer element of an imaging system similar to that of FIG. 16, but illustrating an optical sensor according to another embodiment of the present disclosure.

Referring now to FIGS. 16 and 17, shown therein are exemplary embodiments of optical and/or optoelectronic monitors according to aspects of the present disclosure. In that regard, there are many types of optoelectronic sensors available at a range of sizes suitable for use within the imaging systems of the present disclosure. For example, ambient light sensors, infra-red (IR) sensors, color sensors, light-to-voltage converters, light-to-frequency converters, linear sensor arrays and reflective light sensors may be utilized in accordance with embodiments of the present disclosure.

Referring more specifically to FIG. 16, shown therein is an optical monitor 230 according to an embodiment of the present disclosure. The optical monitor 230 includes an emitter 232 (such as a light emitting diode (LED)) that sends light along path 234 toward the motion profile of transducer 108. The optical monitor 230 also includes a receiver 236 (such as an optoelectronic sensor) that receives reflected light from the motion profile of the transducer 108 along a path 238. In that regard, at least the receiver 236 is in communication with the imaging system such that the signals generated by the receiver 236 can be communicated to a portion of the imaging system for processing. In the illustrated embodiment, the optical monitor 230 is oriented to detect if and when the transducer 108 reaches the ending orientation represented by axis 128. When the transducer 108 interrupts the light path 234, light is reflected back along path 238 to receiver 236. Accordingly, when the receiver 236 receives such reflected light the system can recognize that the transducer 108 has reached the ending orientation, which is indicative of reaching the full field of view. In that regard, the receiver 236, or the associated processor within the imaging system, is designed to identify certain patterns and intensities associated with the transducer reaching the ending orientation of the motion profile. Accordingly, the optical monitor 230 can operate in a binary manner.

Alternatively, in other embodiments the optical monitor 230 is oriented such that it can track the position of the transducer 108 along at least a portion of the motion profile in addition to the ending orientation. For example, in some instances the optical monitor 230 is configured to continuously track the position of the transducer 108 along a majority of the motion profile, including the entire motion profile in some embodiments. In such embodiments, the optical monitor 230 can produce a linear control signal, where the control signal is based on the relative position of the transducer 108 along its motion profile. In some instances, the position of the transducer 108 is measured relative to the ending orientation of a desired motion profile. Further, in some instances, the optical monitor 230 is configured to track the position of the transducer 108 relative to a plurality of discrete points along the motion profile.

Referring now specifically to FIG. 17, shown therein is an optical monitor 240 according to another embodiment of the present disclosure. In many regards, the optical monitor 240 functions in a similar manner to optical monitor 230 discussed above. Accordingly, a detailed discussion of the operation of optical monitor 240 will not be provided. However, as shown in FIG. 17, optical monitor 240 includes an optical fiber 242 that functions as both the emitter and receiver. In that regard, the optical fiber 242 sends light along path 244 toward the motion profile of transducer 108 and receives reflected light from the motion profile of the transducer 108 along a path 246. The optical monitor 240 requires only a single optical fiber adjacent the distal end of the elongated member, allowing for the optical monitor to occupy a very small profile in the housing.

Figure 18:
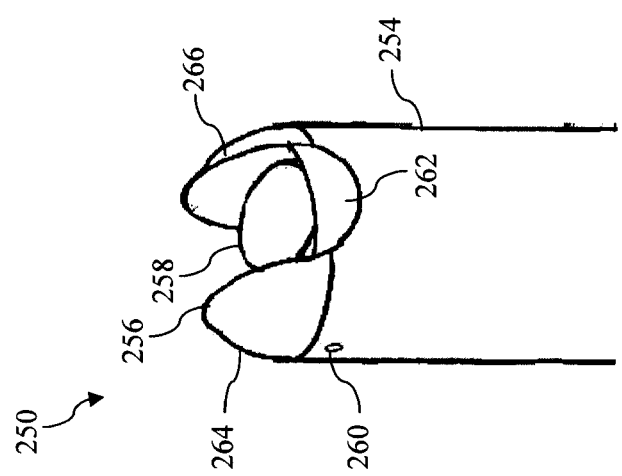
FIG. 18 is a diagrammatic perspective view of a distal end portion of an elongated member that includes an acoustic target according to an embodiment of the present disclosure.

Referring now to FIG. 18, shown therein is a distal portion of an elongated member 250 according to an embodiment of the present disclosure. The distal portion of the elongated member 250 includes a housing 254 extending to a distal tip 256. Further, an ultrasound transducer 258 is positioned within the distal portion of the elongated member 250 and pivots about a pivot pin 260. The elongated member 250 also includes an acoustic target 262 positioned between arms 264 and 266. In the illustrated embodiment, the acoustic target 262 is positioned such that when the ultrasound transducer 258 reaches the ending orientation of its motion profile the acoustic target 262 is within the visible field of the ultrasound transducer 258. In that regard, when the acoustic target 262 is within the visible field or frame of the ultrasound transducer 258 the acoustic target 262 is identifiable as an acoustic signal. In that regard, the acoustic target 262 is formed from a material having a high acoustic reflectivity and, in some instances, the acoustic target 262 has an easily recognizable shape, such as a simple geometrical profile. Accordingly, a processor receiving data from the ultrasound transducer 258 can determine whether the acoustic target 262 is present in any particular image or set of images. Accordingly, the system can recognize when the ultrasound transducer 258 reaches the full field of view.

Further, while the acoustic target 262 has been described in the context of an ultrasound transducer 258, it is understood that a similar concept may be employed with an optical or optoelectronic sensor. In that regard, instead of an acoustic target a visual target that is identifiable by the optical sensor may be utilized. Further still, in some instances a plurality of acoustic targets 262 are utilized at discrete points along the motion profile of the transducer, including but not limited to the starting orientation, the mid-point orientation, the ending orientation, and/or points in between.

The monitors of the present disclosure are suitable for use in a wide variety of catheters, guidewires, and other elongate imaging devices having medical applications. In that regard, the monitors are incorporated into imaging devices having forward looking and/or side-looking capabilities in some instances. That is, the monitors are incorporated into imaging devices that are configured to image generally along the longitudinal axis of the imaging device (i.e., forward-looking) and/or generally perpendicular to the longitudinal axis of the imaging device (i.e., side-looking). Further, in some instances the monitors are incorporated into imaging devices that are configured to image at an oblique angle (either distally or proximally) relative to the longitudinal axis of the imaging device.

Combinations of one or more of the embodiments of monitors described above can also be used. The small size and relative simplicity of the monitors described herein make it possible to manufacture the monitors in a miniature scale such that not only one, but two or more monitors fit inside a catheter or guidewire ranging from 0.5 Fr (0.16 mm, 0.006 inches) up to 12 Fr (4 mm, 0.1 inches) or larger in outside diameter or cross-sectional width. For example, in some particular embodiments the feedback mechanisms of the present disclosure are incorporated into guidewires having a diameter of 0.011 inches or a diameter of 0.014 inches.

Figure 19:
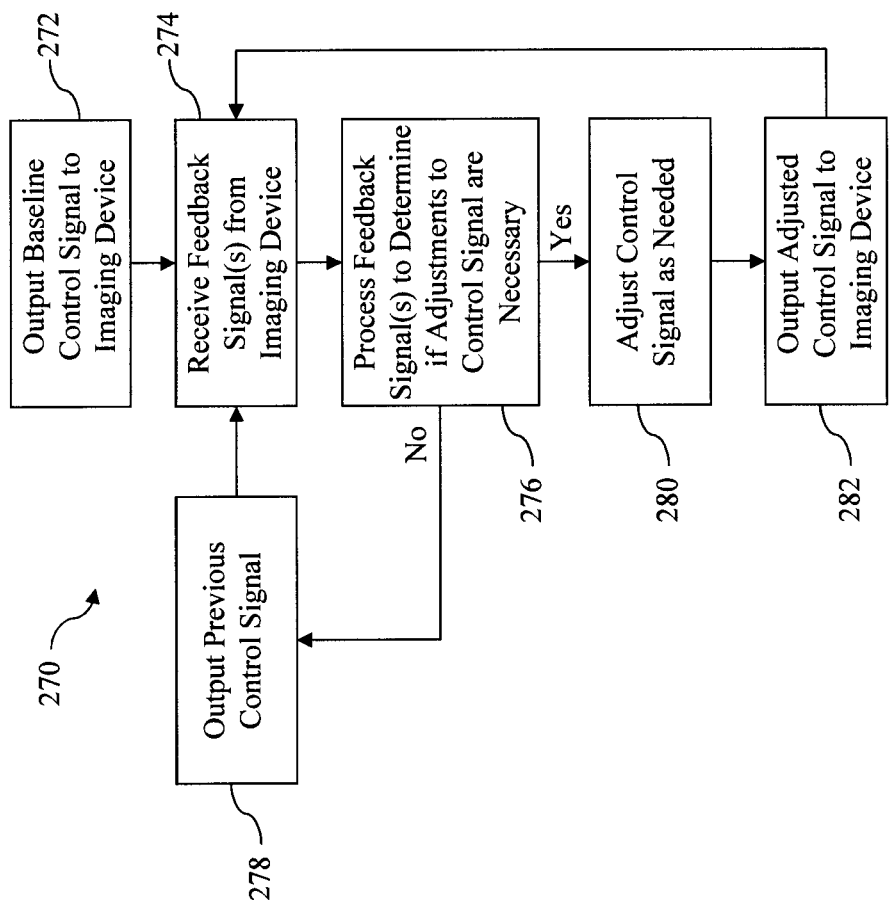
FIG. 19 is a flow chart illustrating a method of controlling a control signal of an imaging system according to an embodiment of the present disclosure.

Referring now to FIG. 19, shown therein is a flow chart illustrating a method 270 of controlling a control signal of an imaging system according to an embodiment of the present disclosure. In that regard, the method 270 utilizes the data obtained using one or more of the monitors described above to provide a feedback control for more consistent scanning and accurate imaging. In that regard, the method 270 begins at step 272 with the imaging system providing a baseline control signal to the imaging device, such as the elongated members discussed above. At step 274, feedback signals are received from the imaging device. In that regard, the feedback signals are the signals received from the monitors described above. Accordingly, in some instances the feedback signals are representative of the position of the transducer along the motion profile. In that regard, the feedback signals may be binary or linear. In some instances, the system utilizes a binary feedback signal as a linear input control variable for a closed-loop system. At step 276, the feedback signals are processed to determine if any adjustments to the control signal are necessary. If not, then the method 270 continues to step 278 where the previous control signal is output to the imaging device again. However, if adjustments to the control signal are necessary, then the method 270 continues to step 280 where the control signal is adjusted based on the feedback signals received from the imaging device at step 274. With the appropriate correction to the control signal calculated at step 280, the adjusted control signal is output to the imaging device at step 282. Then the method 270 continues at step 274 where the feedback signals based on the adjusted control signal are received. This iterative process continues during the operation of the imaging system to provide a consistent transducer motion profile that, in turn, provides accurate imaging.

Figure 20:
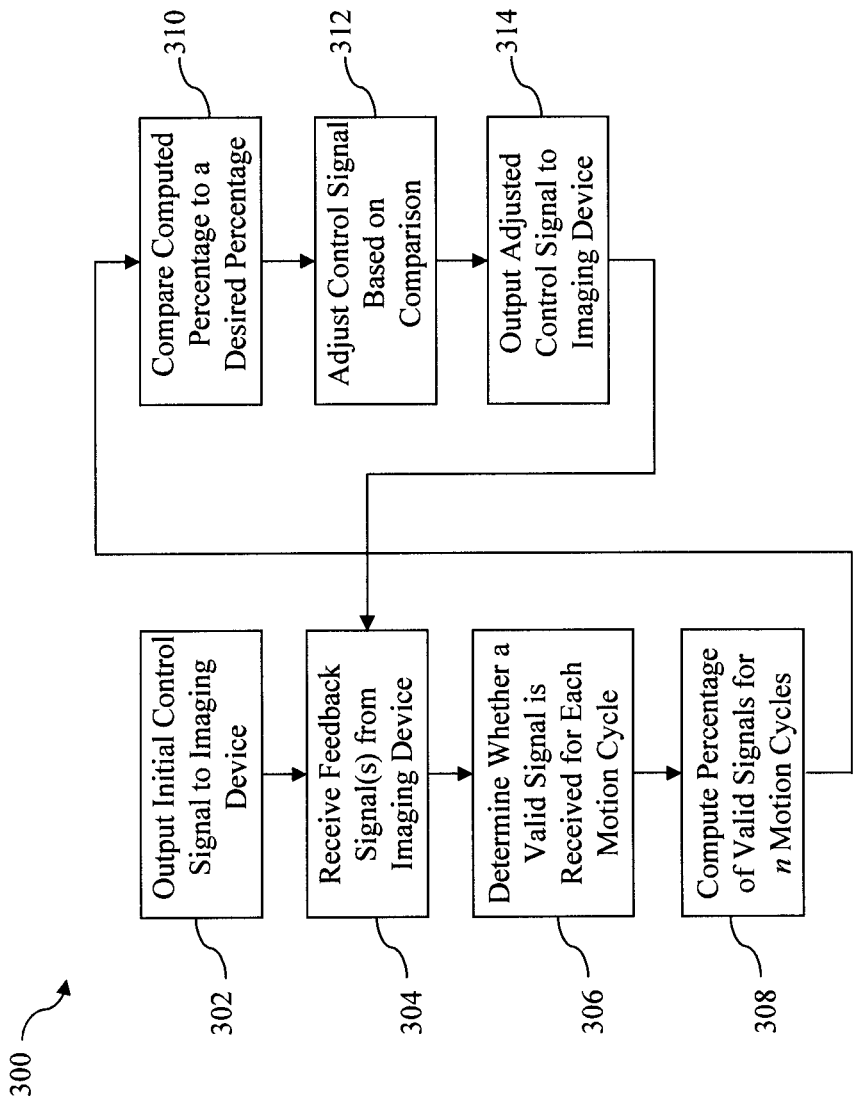
FIG. 20 is a flow chart illustrating a computed percentage method of controlling a control signal of an imaging system according to an embodiment of the present disclosure.

Referring now to FIG. 20, shown therein is a flow chart illustrating a computed percentage method 300 of controlling a control signal of an imaging system according to an embodiment of the present disclosure. As a general matter, the computed percentage method utilizes the percentage of cycles in which a valid binary signal is detected indicating that the transducer reached the ending orientation of the motion profile. In that regard, the system utilizes the percentage of cycles reaching the ending orientation as a linear control variable in governing the motion of the transducer element. The computed percentage method is particularly well-suited for an imaging system or device that has excellent resolution in transducer motion control but significant variance in transducer motion. That is, the system has good control over the transducer motion on average, but may have a good amount of variance around the average for any particular cycle of the motion profile.

The method 300 begins at step 302 where an initial control signal is sent to the imaging device. At step 304, feedback signals are received from the imaging device. At step 306, the system determines whether a valid signal is received for each motion cycle. At step 308, the percentage of valid signals received for a given number (n) motion cycles is calculated. In that regard, the number of motion cycles should be enough to account for the variance in individual motion cycles. Accordingly, in some instances the number of motion cycles is between 2 cycles and 100,000 cycles and may be between 10 cycles and 1,000 cycles. At step 210, the computed percentage of valid signals is compared to a desired percentage of valid signals. In that regard, the desired percentage of valid signals is set based on the desired motion profile of the transducer in some instances. The desired percentage is stored in memory accessible to the system to facilitate the comparison. Generally, the desired percentage is a percentage between 30% and 90% and, in some instances, is a percentage between 50% and 80%. However, in some embodiments, the desired percentage may be outside of these ranges (i.e., greater than 90% or less than 30%). It is understood that, in some instances, the desired percentage is not a single percentage (e.g., 50%), but rather is a percentage range (e.g., between 40% and 60%).

At step 312, the control signal is adjusted, as necessary, based on the comparison. In that regard, if the computed percentage matches the desired percentage match or is within the desired percentage range, then no adjustment is made to the control signal. However, if the computed percentage is less than the desired percentage, then the voltage/current of the control signal is increased to increase the range of motion of the transducer. Similarly, if the computed percentage is greater than the desired percentage, then the voltage/current of the control signal is decreased to decrease the range of motion of the transducer. The relative difference between the desired percentage and the calculated percentage determines the amount of change in the control signal. In that regard, the system utilizes a conversion factor to equate a percentage difference to a corresponding change in the control signal to achieve a desired motion control adjustment. Finally, at step 314 the adjusted control signal is output to the imaging device and the process continues at step 304 where feedback signals are received from the imaging device. This iterative process for controlling the control signal of the imaging system continues during the operation of the imaging system to optimize performance of the system.

Figure 21:
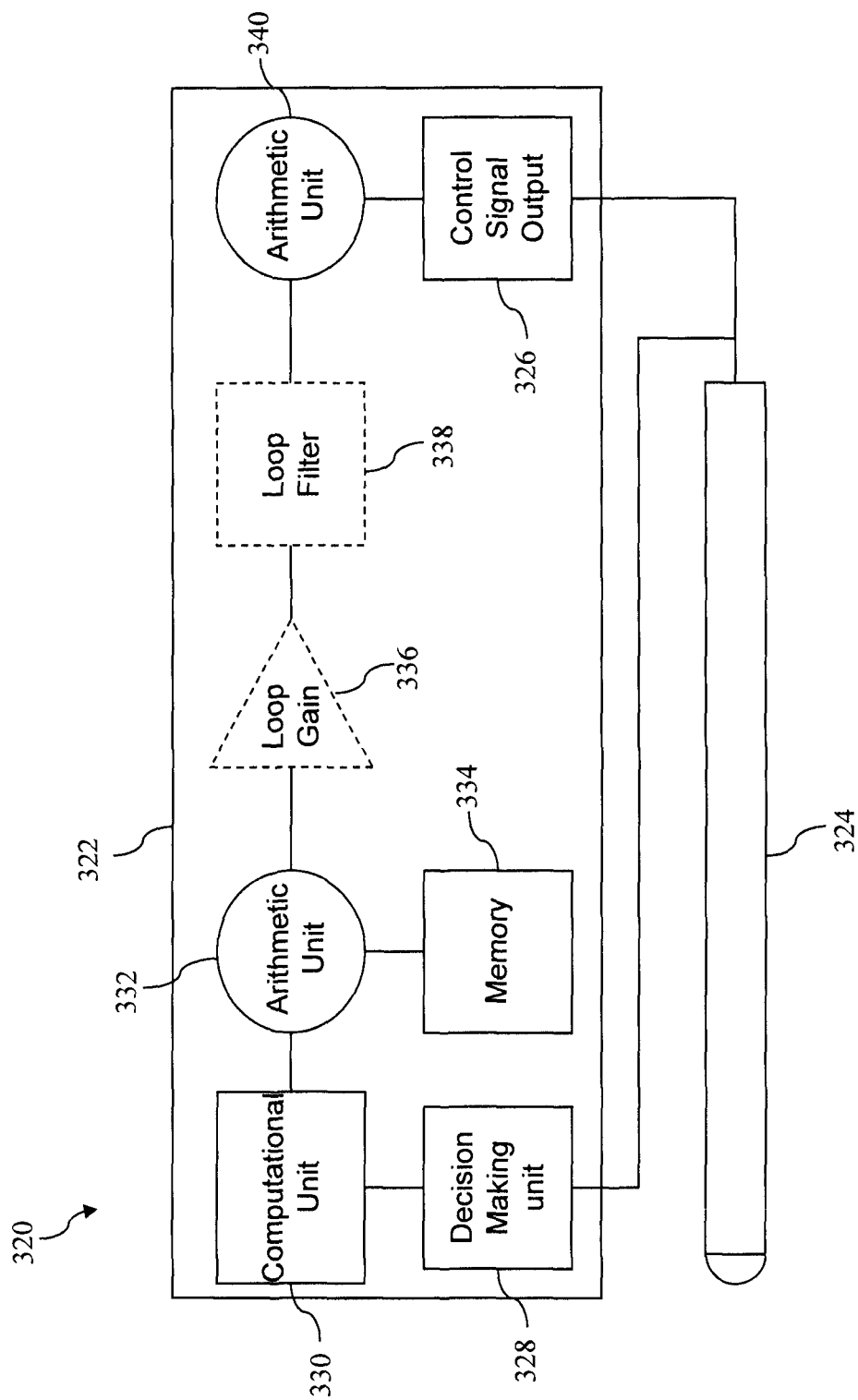
FIG. 21 is a diagrammatic schematic view of a portion of an imaging system according to an embodiment of the present disclosure configured for implementing one or more of the methods of controlling a control signal of the present disclosure.

Referring now to FIG. 21, shown therein is a diagrammatic schematic view of a portion of an imaging system 320 according to an embodiment of the present disclosure. In that regard, the illustrated portion of the imaging system 320 is configured for implementing one or more of the methods of controlling a control signal of the present disclosure. However, for sake of clarity the components of the imaging system 320 will be discussed in the context of the computed percentage method 300 described above in detail.

As shown, the imaging system 320 includes a controller 322 and an imaging device 324. The controller 322 has a control signal output 326 that sends a control signal to the imaging device 324. The controller 322 also receives feedback signals from the imaging device. In that regard, the controller 322 includes a decision making unit 328 that receives the feedback signals from the imaging device. The decision making unit 328 makes a binary determination of whether a valid signal has been received over a cycle time period. A computational unit 330 is in communication with the decision making unit 328. The computational unit 330 computes the percentage of cycles for which valid signals have been received. An arithmetic unit 332 in communication with the computational unit 330 compares the computed percentage provided by the computational unit to a desired percentage. In that regard, the desired value is stored in memory 334 that is accessible to the arithmetic unit 332. In that regard, the desired percentage is optionally set and/or modified by the user in some instances. The controller 322 optionally includes a loop gain 336 and/or a loop filter 338, as indicated by the components being illustrated in phantom. The controller 322 also includes an arithmetic unit 340 that determines the appropriate adjustment to the control signal based on the difference between the computed percentage and the desired percentage. In that regard, the arithmetic unit 340 keeps track of the control adjustments over time in order to provide a cumulative control adjustment. It is understood that the imaging system and, in particular, the controller 322 may include any number of other electronic components and/or circuitry not shown in FIG. 21. Further, it is understood that the various components of the controller 322 described above may be implemented in hardware, software, firmware, and/or combinations thereof. In that regard, it is also understood that two or more of the various components of the controller 322 described above may be combined into a single hardware or software component. Likewise, it is understood that a single component of the controller 322 described above may be split into two or more hardware or software components. Further, it is understood that the components of the controller 322 need not be positioned within a single chassis, but instead may be positioned in separate housings and/or be positioned remote from one another. In that regard, it is understood that components of the system may communicate through wired and/or wireless protocols, including communications requiring connection over a network.

Figure 22:
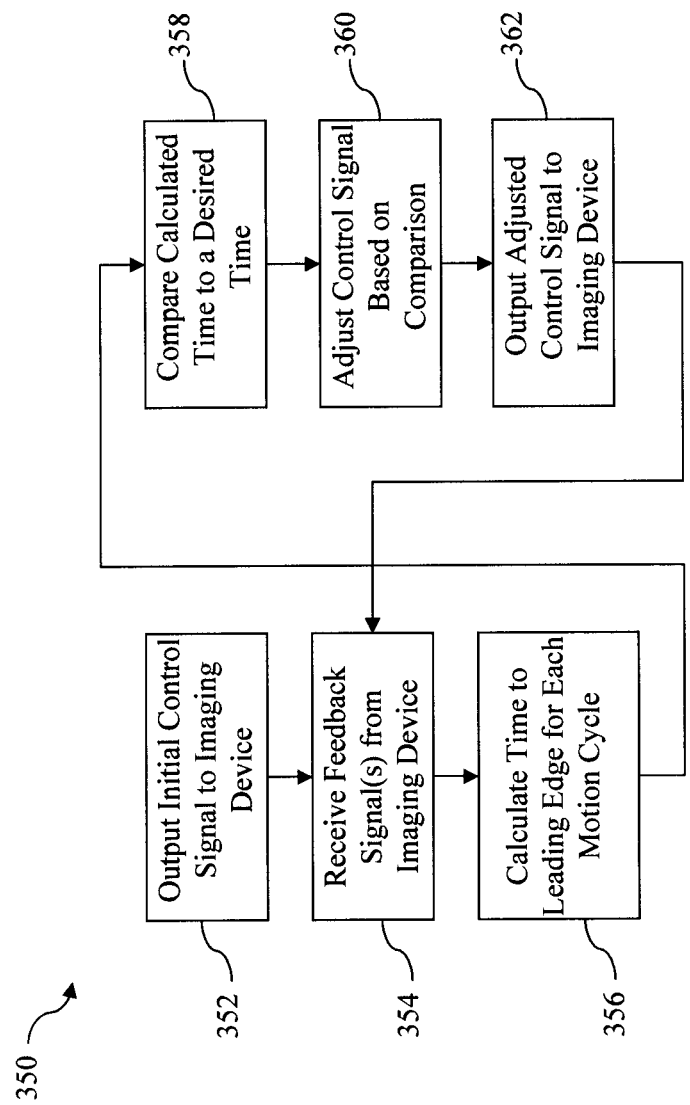
FIG. 22 is a flow chart illustrating a method of controlling a control signal of an imaging system based on timing of feedback signals according to an embodiment of the present disclosure.
Figure 23:
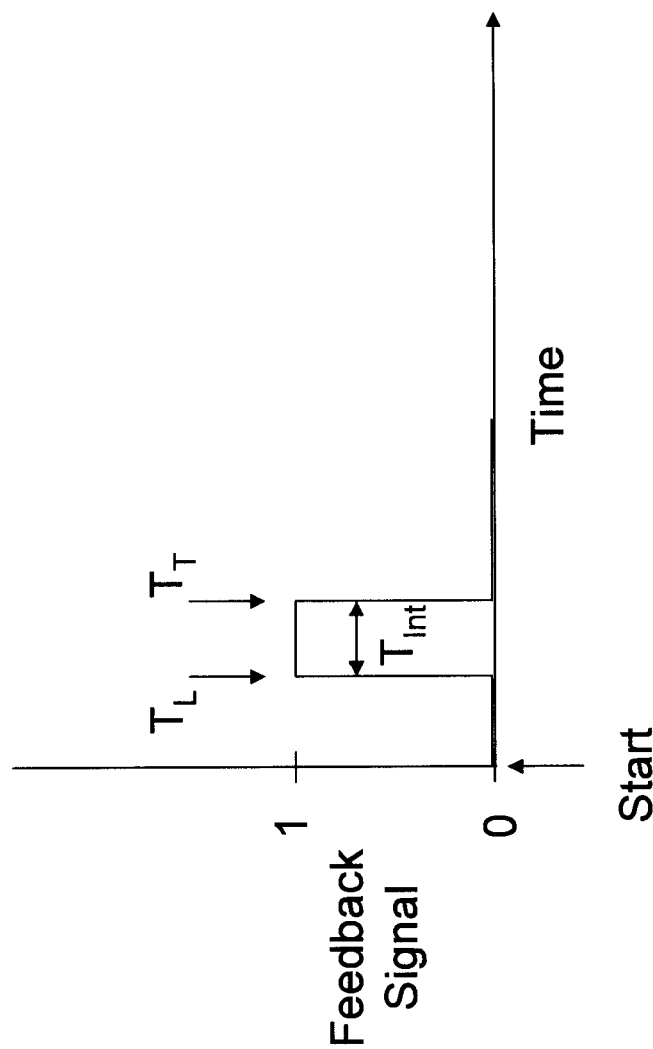
FIG. 23 is a graph mapping a feedback signal of an imaging system over time according to an embodiment of the present disclosure.
Figure 24:
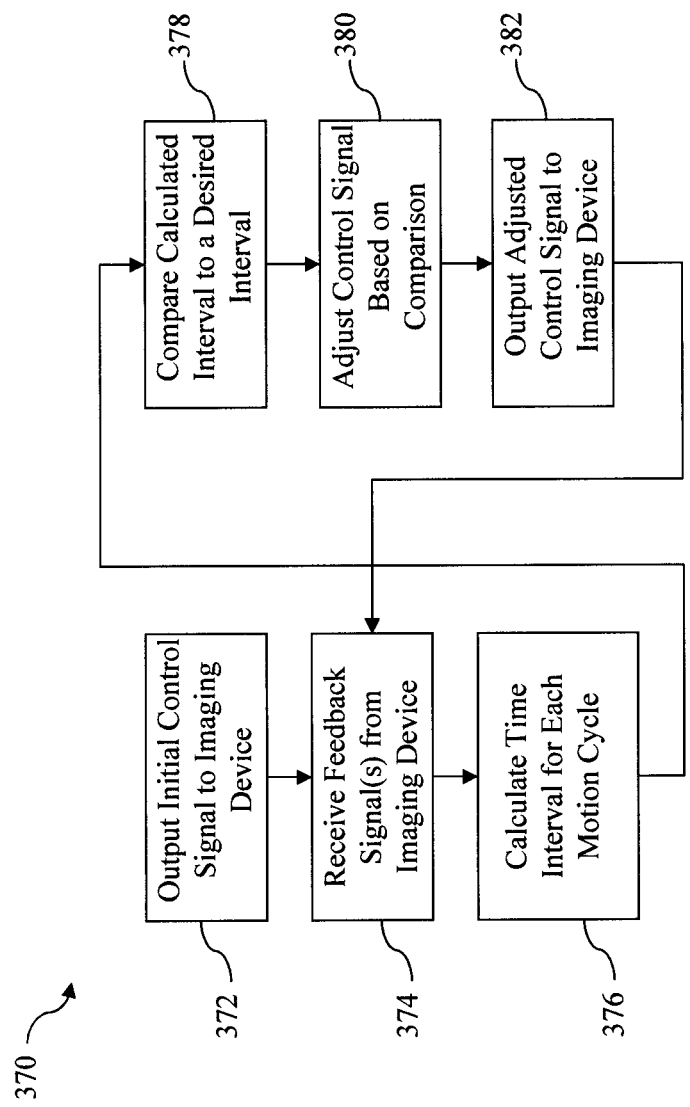
FIG. 24 is a flow chart illustrating a method of controlling a control signal of an imaging system based on timing of feedback signals according to another embodiment of the present disclosure.

Referring now to FIGS. 22-24, methods of controlling a control signal of an imaging system based on timing of feedback signals will be discussed. With respect to FIG. 22, a method 350 of controlling a control signal based on the measured time to a leading edge of a feedback signal will be described. In that regard, the method generally measures the time from the start of a motion cycle until the leading edge of a valid binary feedback signal is detected. This measured time is utilized as a linear control variable in governing the motion of the transducer element. This time to leading edge method is particularly well-suited for an imaging system or device where the transducer position as a function of time is monotonic (e.g., always moving left or right) and is a function that can be uniformly compressed and decompressed in time.

The method 350 begins at step 352 where an initial control signal is sent to the imaging device. At step 354, feedback signals are received from the imaging device. At step 356, the system calculates the amount of time to the leading edge for each motion cycle. In that regard, FIG. 23 illustrates an exemplary graph of a feedback signal over time for an imaging system. In that regard, the motion cycle begins at time=0. As shown, the binary feedback signal is at 0 initially because the transducer has not reached the ending orientation of the motion profile. However, at time $T_L$ (or time to leading edge) the binary feedback signal becomes 1, indicating that the transducer has reached the ending orientation of its motion profile. At time $T_T$ (or time to trailing edge) the binary feedback signal returns to 0, indicating that the transducer is no longer at the ending orientation and is returning back along its motion profile towards the starting orientation. In that regard, the amount of time the binary feedback signal is at 1 is indicated by time $T_{INT}$ (or time interval). In accordance with the present disclosure, an algorithm or other calculated determination utilizes one or more of the $T_L$, $T_T$, and $T_{INT}$ as a control variable(s) to determine the necessary adjustment to the control signal. In that regard, the system reaches a steady state when the resulting $T_L$, $T_T$, $T_{INT}$, and/or combinations thereof matches a pre-determined value.

In that regard, referring again to FIG. 22, at step 358, the calculated time is compared to a desired time. In that regard, the desired time is set based on the desired motion profile of the transducer in some instances. The desired time is stored in memory accessible to the system to facilitate the comparison. In some instances, the desired time is between 1 millisecond and 20 milliseconds and may be between 4 milliseconds and 10 milliseconds. However, in some embodiments, the desired time may be outside of these ranges (i.e., less than 1 millisecond or more than 20 milliseconds). It is understood that, in some instances, the desired time is not a specific amount of time (i.e., 8 milliseconds), but rather is a timeframe (e.g., between 4 milliseconds and 10 milliseconds).

At step 360, the control signal is adjusted, as necessary, based on the comparison. The relative difference between the desired time and the calculated time determines the amount of change in the control signal. Finally, at step 362 the adjusted control signal is output to the imaging device and the process continues at step 354 where feedback signals are received from the imaging device. This iterative process for controlling the control signal of the imaging system continues during the operation of the imaging system to optimize performance of the system.

Referring now to FIG. 24, shown therein is a flow chart illustrating a method 370 of controlling a control signal of an imaging system based on timing of feedback signals according to another embodiment of the present disclosure. This time interval method is particularly well-suited for an imaging system or device that has naturally low deceleration and acceleration at the boundaries of the transducer motion profile. The method 370 begins at step 372 where an initial control signal is sent to the imaging device. At step 374, feedback signals are received from the imaging device. At step 376, the system calculates the amount of the time interval ($T_{INT}$) of a valid feedback signal for each motion cycle. At step 378, the calculated time interval is compared to a desired time interval. In that regard, the desired time interval is set based on the desired motion profile of the transducer in some instances. The desired time interval is stored in memory accessible to the system to facilitate the comparison. In some instances, the desired time interval is between 1 microsecond and 1 millisecond. However, in some embodiments, the desired time interval may be outside of this range (i.e., less than 1 microsecond or more than 1 millisecond). It is understood that, in some instances, the desired time interval is not a specific amount of time (i.e., 6 microseconds), but rather is a timeframe (e.g., between 4 microseconds and 8 microseconds).

At step 380, the control signal is adjusted, as necessary, based on the comparison. The relative difference between the desired time interval and the calculated time interval determines the amount of change in the control signal. Finally, at step 382 the adjusted control signal is output to the imaging device and the process continues at step 374 where feedback signals are received from the imaging device. This iterative process for controlling the control signal of the imaging system continues during the operation of the imaging system to optimize performance of the system.

Utilizing the monitors and/or feedback control loops described above, scanning mechanism performance can be adjusted in real time to account for device to device variation. In that regard, there are several parameters that contribute to the device to device variation, such as actuator shaft friction, actuator return spring, pre-loading of transducer return spring, transducer height and diameter and housing friction. While effort is made to reduce the variations among these parameters during manufacturing and assembly, it is not possible to completely eliminate the variation. As a result, a time consuming characterization step is typically necessary for every completed imaging device/system in order to determine the scanning performance variation (e.g. scan time, scan velocity) of that particular device/system. In addition to the time it takes to characterize the device/system, the information specific to that device/system must be stored, tracked, and used to run that specific device/system in the future. By utilizing one or more of the monitors and associated feedback loops described above, the need for characterization and device/system specific information tracking can be eliminated or significantly reduced as the feedback loops themselves provide the necessary calibration of the device/system to ensure optimized imaging performance. In that regard, as described above, the feedback mechanisms of the present disclosure can adjust scanning parameters, such as actuator current or actuator current wave form, on the fly to compensate variations. As a result, any variation that exists between devices (or within a single device over time) is accounted for and adjusted for in real time as the device is used.

Further, the monitors and feedback control loops of the present disclosure are also suitable for reducing image jitter. Image jitter is defined as the variation in the scan angle vs. time between two consecutive frames or groups of consecutive frames. Jitter can a result of slight changes in the thermal environment or friction experienced during consecutive scans. These variations can be accounted for and compensated for in real time using the feedback mechanisms of the present disclosure. In that regard, by keeping track of a number of parameters (individually or in combination) the image can be adjusted in real time to reduce or eliminate the jitter or the scan angle vs. time variation between two consecutive frames. The tracked parameters may include one or more of the $T_L$, $T_T$, $T_{INT}$, location of an acoustic target, any of the parameters discussed with respect to the monitors and feedback control loops above, and/or combinations thereof. Accordingly, the current driving the actuator is adjusted for each scan cycle or group of scan cycles to dynamically remove the jitter in order to maintain a steady image. In some instances, the information obtained from the feedback mechanism for a scan, a previous scan, or an average of several scans is utilized to shift acoustic line data to a different angular position in order to reduce jitter effects.

Image jitter is also a function of scan angle. In that regard, the last portions of a scan tend to suffer from increased image jitter as compared to the portions of the scan that preceded it. Accordingly, one way to address this issue is to disregard the last portions of a scan, such as the last 1, 5, 10, 15, 20, 25, 30, 35 degrees, or a range defined by two of these values. By not displaying the last portions of the scan, the most problematic jitter area is eliminated. Accordingly, by overdriving the scanning mechanism by the amount of scan angle that will not be displayed to the user, the full field of view is provided to the user without the jitter problems associated with the last portions of the scan. In that regard, the feedback control mechanisms described above can be utilized to monitor the amount of scan overdrive and adjust it as necessary. For example, in one embodiment the time to leading edge method (discussed above with respect to FIG. 22) is utilized to verify that scanning is being overdriven at the appropriate level.

Figure 25:
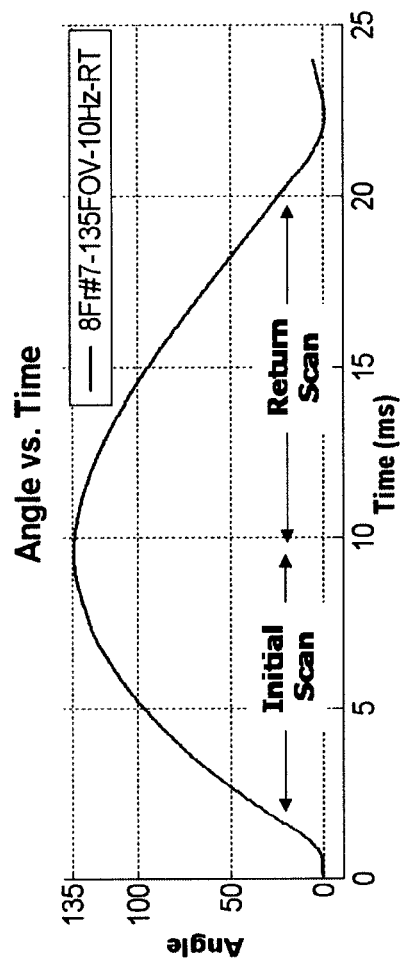
FIG. 25 is a graph illustrating the angular motion of a transducer of an imaging system over time according to an embodiment of the present disclosure.

Further still, referring now to FIG. 25, the feedback control mechanisms of the present disclosure can also be utilized to activate the imaging transducer on the return path (i.e., the motion path from the ending orientation to the starting orientation). In that regard, FIG. 25 is a graph illustrating the angular motion of a transducer of an imaging system over time. As shown, the return path is generally 30-40% longer than the initial path and the maximum velocity of the transducer along the return path can be 50% slower. In some embodiments, the return velocity is independent of the original actuation step and frame rate, as it is completely dependent on the transducer torsion spring constant that causes the transducer to return to its start position. The highest velocity in the return path is at the end of the scan and not in the middle of the FOV as is the case in the initial scan. Since the return scan velocity is dominated by the transducer spring constant in the embodiment shown, actuator variation effects can be eliminated or reduced by imaging on the return scan.

The exact time that the return scan begins is often difficult to determine due to jitter. Therefore, it is difficult to know when to start obtaining images on the return scan. However, this problem can be overcome by utilizing the feedback control mechanisms described above. In particular, the return scan imaging can be triggered when the monitor indicates that the transducer has reached the ending orientation of the motion profile, thereby indicating that the transducer is starting along the return path.

Although the present disclosure has been described primarily in connection with the use of imaging transducers (e.g., ultrasound transducers), it should be appreciated that the present disclosure can be utilized in other medical devices in which it is desired to provide diagnostic and/or therapeutic procedures utilizing rapid oscillatory motion.

Although illustrative embodiments have been shown and described, a wide range of modification, change, and substitution is contemplated in the foregoing disclosure and in some instances, some features of the present disclosure may be employed without a corresponding use of the other features. It is understood that such variations may be made in the foregoing without departing from the scope of the present disclosure. Accordingly, it is appropriate that the appended claims be construed broadly and in a manner consistent with the scope of the present disclosure.

What is claimed is:

1. A method of imaging an internal structure of a patient from within the internal structure, the method comprising:
   communicating a control signal to an actuator of an imaging device, the actuator causing oscillation of a movable component of an imaging apparatus positioned in a distal portion of the imaging device to image the internal structure of the patient based on the control signal;
   receiving a feedback signal from a monitor positioned in the distal portion of the imaging device, the feedback signal being representative of a position of the movable component;
   processing the feedback signal;
   adjusting an aspect of the control signal based on processing the feedback signal; and
   communicating the adjusted control signal to the actuator of the imaging device;
   wherein the feedback signal is representative of the movable component reaching a boundary of a motion profile of the imaging apparatus,
   wherein receiving the feedback signal comprises receiving a binary signal,
   wherein the monitor is a switch, and
   wherein processing the feedback signal comprises:
   determining whether the binary signal is valid for each motion cycle of the imaging apparatus;
   calculating a percentage of motion cycles with valid signals for n motion cycles; and
   comparing the calculated percentage to a desired percentage.

2. The method of claim 1, wherein adjusting the aspect of the initial control signal based on processing the feedback signal includes:
   increasing a drive current of the control signal if the calculated percentage is less than the desired percentage.

3. The method of claim 2, wherein adjusting the aspect of the initial control signal based on processing the feedback signal includes:
   decreasing a drive current of the control signal if the calculated percentage is greater than the desired percentage.

4. The method of claim 1, wherein the motion profile of the movable component is an arc having an angle between about 25 degrees and about 360 degrees.

5. The method of claim 1, wherein the imaging apparatus is comprised of an imaging transducer.

6. The method of claim 1, wherein the imaging apparatus is comprised of a reflective element.

7. The method of claim 1, wherein the steps of communicating a control signal to the actuator, receiving a feedback signal from the monitor, processing the feedback signal; adjusting an aspect of the control signal, and communicating the adjusted control signal are utilized to calibrate the imaging device.

8. The method of claim 1, wherein the steps of adjusting an aspect of the control signal and communicating the adjusted control signal to the actuator reduces image jitter in images provided by the imaging device.

9. The method of claim 1, wherein the internal structure being imaged is selected from the group consisting of an artery, a vein, a neurovascular structure, a heart chamber, a heart valve, a gastrointestinal track, and a bronchial.

10. A method of imaging an internal structure of a patient from within the internal structure, the method comprising:
    communicating a control signal to an actuator of an imaging device, the actuator causing oscillation of a movable component of an imaging apparatus positioned in a distal portion of the imaging device to image the internal structure of the patient based on the control signal;
    receiving a feedback signal from a monitor positioned in the distal portion of the imaging device, the feedback signal being representative of a position of the movable component;
    processing the feedback signal;
    adjusting an aspect of the control signal based on processing the feedback signal; and communicating the adjusted control signal to the actuator of the imaging device;
    wherein the feedback signal is representative of the movable component reaching a boundary of a motion profile of the imaging apparatus,
    wherein receiving the feedback signal comprises receiving a binary signal,
    wherein the monitor is a switch, and
    wherein processing the feedback signal comprises:
    measuring an elapsed time from a beginning of a motion cycle to a leading edge of the feedback signal for the motion cycle of the imaging apparatus;
    comparing the measured elapsed time to a desired elapsed time.

11. The method of claim 10, wherein adjusting the aspect of the initial control signal based on processing the feedback signal includes:
    increasing a drive current of the control signal if the measured elapsed time is greater than the desired elapsed time.

12. The method of claim 10, wherein the imaging apparatus is comprised of an imaging transducer.

13. The method of claim 10, wherein the imaging apparatus is comprised of a reflective element.

14. The method of claim 10, wherein the steps of communicating a control signal to the actuator, receiving a feedback signal from the monitor, processing the feedback signal; adjusting an aspect of the control signal, and communicating the adjusted control signal are utilized to calibrate the imaging device.

15. The method of claim 10, wherein the steps of adjusting an aspect of the control signal and communicating the adjusted control signal to the actuator reduces image jitter in images provided by the imaging device.

16. The method of claim 10, wherein the internal structure being imaged is selected from the group consisting of an artery, a vein, a neurovascular structure, a heart chamber, a heart valve, a gastrointestinal track, and a bronchial.

17. A method of imaging an internal structure of a patient from within the internal structure, the method comprising:
    communicating a control signal to an actuator of an imaging device, the actuator causing oscillation of a movable component of an imaging apparatus positioned in a distal portion of the imaging device to image the internal structure of the patient based on the control signal;

receiving a feedback signal from a monitor positioned in the distal portion of the imaging device, the feedback signal being representative of a position of the movable component;

processing the feedback signal;

adjusting an aspect of the control signal based on processing the feedback signal; and communicating the adjusted control signal to the actuator of the imaging device;

wherein the feedback signal is representative of the movable component reaching a boundary of a motion profile of the imaging apparatus, wherein receiving the feedback signal comprises receiving a binary signal, wherein the monitor is a switch, and wherein processing the feedback signal comprises:

measuring a time interval from a leading edge of the feedback signal to a trailing edge of the feedback signal for a motion cycle of the imaging apparatus;

comparing the measured time interval to a desired time interval.

18. The method of claim 17, wherein the imaging apparatus is comprised of an imaging transducer.

19. The method of claim 17, wherein the imaging apparatus is comprised of a reflective element.

20. The method of claim 17, wherein the steps of communicating a control signal to the actuator, receiving a feedback signal from the monitor, processing the feedback signal; adjusting an aspect of the control signal, and communicating the adjusted control signal are utilized to calibrate the imaging device.

21. The method of claim 17, wherein the steps of adjusting an aspect of the control signal and communicating the adjusted control signal to the actuator reduces image jitter in images provided by the imaging device.

22. The method of claim 17, wherein the internal structure being imaged is selected from the group consisting of an artery, a vein, a neurovascular structure, a heart chamber, a heart valve, a gastrointestinal track, and a bronchial.

* * * * *